US012758705B2

(12) United States Patent
Breingan et al.

(10) Patent No.: US 12,758,705 B2
(45) Date of Patent: Oct. 13, 2026

(54) FLEXIBLE LINKAGE FOR POSITIVE DISPLACEMENT PUMPS

(71) Applicant: INSULET CORPORATION, Acton, MA (US)

(72) Inventors: Kyle Breingan, Lowell, MA (US); Orlando Cossia Castiglioni, Boston, MA (US)

(73) Assignee: INSULET CORPORATION, Acton, MA (US)

( * ) Notice: Subject to any disclaimer, the term of this patent is extended or adjusted under 35 U.S.C. 154(b) by 621 days.

(21) Appl. No.: 18/047,072

(22) Filed: Oct. 17, 2022

(65) Prior Publication Data

US 2023/0122652 A1 Apr. 20, 2023

Related U.S. Application Data

(60) Provisional application No. 63/256,712, filed on Oct. 18, 2021.

(51) Int. Cl.
*A61M 5/145* (2006.01)
*A61M 5/142* (2006.01)

(52) U.S. Cl.
CPC ...... *A61M 5/1452* (2013.01); *A61M 5/14244* (2013.01); *A61M 2005/14506* (2013.01); *A61M 2205/0266* (2013.01); *A61M 2205/103* (2013.01)

(58) Field of Classification Search
CPC ........ A61M 2005/14506; A61M 5/145; A61M 5/1452; A61M 2005/14533; A61M 5/1454; A61M 5/14586; A61M 2205/0266; A61M 2005/31518; A61M 2205/103; A61M 5/14244; A61M 5/14248
See application file for complete search history.

(56) References Cited

U.S. PATENT DOCUMENTS

| | | | |
|---|---|---|---|
| 1,441,508 | A | 1/1923 | Jensen |
| 2,198,666 | A | 4/1940 | Gruskin |
| 2,752,918 | A | 7/1956 | Uytenbogaar |
| 3,176,712 | A | 4/1965 | Ramsden |
| 3,297,260 | A | 1/1967 | Barlow |

(Continued)

FOREIGN PATENT DOCUMENTS

| | | | |
|---|---|---|---|
| CA | 606281 | A | 10/1960 |
| CN | 1375338 | A | 10/2002 |

(Continued)

OTHER PUBLICATIONS

International Search Report and Written Opinion for PCT/US2018/014351, mailed on Jun. 4, 2018, 9 pages.

(Continued)

*Primary Examiner* — Quynh-Nhu H. Vu
(74) *Attorney, Agent, or Firm* — Goodwin Procter LLP

(57) ABSTRACT

A novel embodiment of a pump mechanism, for example, of the type that would be used in a wearable drug delivery system, comprises, in a preferred embodiment, a reservoir, a plunger, disposed within the reservoir and driven by a coiled flexible linkage connected to a drive mechanism, such that a force imparted by the drive mechanism causes the coiled flexible linkage to uncoil, causing a linear translation of the plunger through the reservoir to force a liquid drug contained within the reservoir through a fluid port to a patient.

15 Claims, 9 Drawing Sheets

(56) References Cited

U.S. PATENT DOCUMENTS 3,464,359 A 9/1969 King
3,885,662 A 5/1975 Schaefer
3,946,732 A 3/1976 Hurscham
3,947,692 A 3/1976 Payne
3,993,061 A 11/1976 OLeary
4,108,177 A 8/1978 Pistor
4,152,098 A 5/1979 Moody et al.
4,210,173 A 7/1980 Choksi et al.
4,221,219 A 9/1980 Tucker
4,257,324 A 3/1981 Stefansson et al.
4,268,150 A 5/1981 Chen
4,277,226 A 7/1981 Archibald
4,313,439 A 2/1982 Babb et al.
4,371,790 A 2/1983 Manning et al.
4,417,889 A 11/1983 Choi
4,424,720 A 1/1984 Bucchianeri
4,435,173 A 3/1984 Siposs et al.
4,475,905 A 10/1984 Himmelstrup
4,498,843 A 2/1985 Schneider et al.
4,507,115 A 3/1985 Kambara et al.
4,551,134 A 11/1985 Slavik et al.
4,562,751 A 1/1986 Nason et al.
4,567,549 A 1/1986 Lemme
4,585,439 A 4/1986 Michel
4,601,707 A 7/1986 Albisser et al.
4,634,427 A 1/1987 Hannula et al.
4,671,429 A 6/1987 Spaanderman et al.
4,678,408 A 7/1987 Nason et al.
4,684,368 A 8/1987 Kenyon
4,685,903 A 8/1987 Cable et al.
4,755,169 A 7/1988 Sarnoff et al.
4,766,889 A 8/1988 Trick et al.
4,808,161 A 2/1989 Kamen
4,846,797 A 7/1989 Howson et al.
4,858,619 A 8/1989 Toth
4,898,579 A 2/1990 Groshong et al.
4,908,017 A 3/1990 Howson et al.
4,944,659 A 7/1990 Labbe et al.
4,969,874 A 11/1990 Michel et al.
4,991,743 A 2/1991 Walker
5,007,458 A 4/1991 Marcus et al.
5,020,325 A 6/1991 Henault
5,062,841 A 11/1991 Siegel
5,147,311 A 9/1992 Pickhard
5,178,609 A 1/1993 Ishikawa
5,205,819 A 4/1993 Ross et al.
5,213,483 A 5/1993 Flaherty et al.
5,222,362 A 6/1993 Maus et al.
5,236,416 A 8/1993 McDaniel et al.
5,241,172 A * 8/1993 Lugaresi ................ G01D 5/366 341/13
5,261,882 A 11/1993 Sealfon
5,261,884 A 11/1993 Stern et al.
5,277,338 A 1/1994 Divall et al.
5,281,202 A 1/1994 Weber et al.
5,346,476 A 9/1994 Elson
5,364,342 A 11/1994 Beuchat et al.
5,388,615 A 2/1995 Edlund et al.
5,433,710 A 7/1995 VanAntwerp et al.
5,503,628 A 4/1996 Fetters et al.
5,520,661 A 5/1996 Lal et al.
5,533,389 A 7/1996 Kamen et al.
5,582,593 A 12/1996 Hultman
5,618,269 A 4/1997 Jacobsen et al.
5,628,309 A 5/1997 Brown
5,637,095 A * 6/1997 Nason ............... A61M 5/14244 604/154
5,665,070 A 9/1997 McPhee
5,713,875 A 2/1998 Tanner, II
5,747,350 A 5/1998 Sattler
5,748,827 A 5/1998 Holl et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,807,075 A 9/1998 Jacobsen et al.
5,839,467 A 11/1998 Saaski et al.
5,891,097 A 4/1999 Saito et al.
5,897,530 A 4/1999 Jackson
5,906,597 A 5/1999 McPhee
5,911,716 A 6/1999 Rake et al.
5,919,167 A 7/1999 Mulhauser et al.
5,957,890 A 9/1999 Mann et al.
5,961,492 A 10/1999 Kriesel et al.
5,971,963 A 10/1999 Choi
6,019,747 A 2/2000 McPhee
6,050,457 A 4/2000 Arnold et al.
6,068,615 A 5/2000 Brown et al.
6,159,161 A * 12/2000 Hodosh ................... A61M 5/20 600/561
6,159,188 A 12/2000 Laibovitz et al.
6,174,300 B1 1/2001 Kriesel et al.
6,190,359 B1 2/2001 Heruth
6,200,293 B1 3/2001 Kriesel et al.
6,352,522 B1 3/2002 Kim et al.
6,363,609 B1 4/2002 Pickren
6,375,638 B2 4/2002 Nason et al.
6,474,219 B2 11/2002 Klitmose et al.
6,485,461 B1 11/2002 Mason et al.
6,485,462 B1 11/2002 Kriesel
6,488,652 B1 12/2002 Weijand et al.
6,520,936 B1 2/2003 Mann
6,527,744 B1 3/2003 Kriesel et al.
6,537,249 B2 3/2003 Kriesell et al.
6,537,251 B2 * 3/2003 Klitmose .......... A61M 5/14566 604/131
6,539,286 B1 3/2003 Jiang
6,569,115 B1 5/2003 Barker et al.
6,595,956 B1 7/2003 Gross et al.
6,656,158 B2 12/2003 Mahoney et al.
6,699,218 B2 3/2004 Flaherty et al.
6,723,072 B2 4/2004 Flaherty et al.
6,740,059 B2 5/2004 Flaherty
6,749,407 B2 6/2004 Xie et al.
6,851,260 B2 2/2005 Mernoe
6,854,620 B2 * 2/2005 Ramey ................ A61M 5/1456 222/327
6,883,778 B1 4/2005 Newton et al.
7,018,360 B2 3/2006 Flaherty et al.
7,104,275 B2 9/2006 Dille
7,128,727 B2 10/2006 Flaherty et al.
7,137,964 B2 11/2006 Flaherty
7,160,272 B1 1/2007 Eyal et al.
7,303,549 B2 12/2007 Flaherty
7,771,392 B2 8/2010 De Polo et al.
7,914,499 B2 3/2011 Gonnelli et al.
7,951,114 B2 5/2011 Rush et al.
7,985,201 B2 * 7/2011 Langley .................. A61M 5/20 604/131
8,057,436 B2 * 11/2011 Causey ............. A61M 5/14244 604/151
8,267,921 B2 9/2012 Yodfat et al.
8,382,703 B1 2/2013 Abdelaal
8,499,913 B2 8/2013 Gunter
8,905,995 B2 12/2014 Mernoe
8,920,376 B2 12/2014 Caffey et al.
8,939,935 B2 1/2015 OConnor et al.
9,180,244 B2 11/2015 Anderson et al.
9,192,716 B2 11/2015 Jugl et al.
9,402,950 B2 8/2016 Dilanni et al.
9,539,596 B2 1/2017 Ikushima
10,441,723 B2 10/2019 Nazzaro
10,695,485 B2 6/2020 Nazzaro
2001/0016710 A1 8/2001 Nason et al.
2001/0056258 A1 12/2001 Evans
2002/0004651 A1 * 1/2002 Ljunggreen ........ A61M 5/31511 604/218
2002/0029018 A1 3/2002 Jeffrey
2002/0032374 A1 3/2002 Holker et al.
2002/0037221 A1 3/2002 Mastrangelo et al.
2002/0091358 A1 7/2002 Klitmose
2002/0173769 A1 11/2002 Gray et al.
2002/0173830 A1 11/2002 Starkweather et al.

(56) References Cited

U.S. PATENT DOCUMENTS

| | | | |
|---|---|---|---|
| 2003/0040715 A1 | 2/2003 | DAntonio et al. | |
| 2003/0055380 A1 | 3/2003 | Flaherty | |
| 2003/0097092 A1 | 5/2003 | Flaherty | |
| 2003/0109827 A1 | 6/2003 | Lavi et al. | |
| 2003/0163097 A1 | 8/2003 | Fleury et al. | |
| 2003/0198558 A1 | 10/2003 | Nason et al. | |
| 2003/0199825 A1 | 10/2003 | Flaherty | |
| 2004/0010207 A1 | 1/2004 | Flaherty et al. | |
| 2004/0064088 A1 | 4/2004 | Gorman et al. | |
| 2004/0068224 A1 | 4/2004 | Couvillon, Jr. et al. | |
| 2004/0069044 A1 | 4/2004 | Lavi et al. | |
| 2004/0092865 A1 | 5/2004 | Flaherty et al. | |
| 2004/0094733 A1 | 5/2004 | Hower et al. | |
| 2004/0153032 A1 | 8/2004 | Garribotto et al. | |
| 2005/0020980 A1 | 1/2005 | Inoue et al. | |
| 2005/0165363 A1 | 7/2005 | Judson et al. | |
| 2005/0203461 A1 | 9/2005 | Flaherty et al. | |
| 2005/0238507 A1 | 10/2005 | Dilanni et al. | |
| 2005/0273059 A1 | 12/2005 | Mernoe | |
| 2005/0277882 A1 | 12/2005 | Kriesel | |
| 2006/0041229 A1 | 2/2006 | Garibotto et al. | |
| 2006/0079765 A1 | 4/2006 | Neer et al. | |
| 2006/0155210 A1 | 7/2006 | Beckman et al. | |
| 2006/0173439 A1 | 8/2006 | Thorne et al. | |
| 2006/0178633 A1 | 8/2006 | Garibotto et al. | |
| 2006/0253085 A1 | 11/2006 | Geismar et al. | |
| 2006/0282290 A1 | 12/2006 | Flaherty et al. | |
| 2007/0005018 A1 | 1/2007 | Tekbuchava | |
| 2007/0073236 A1 | 3/2007 | Merno et al. | |
| 2007/0088271 A1 | 4/2007 | Richards | |
| 2007/0118405 A1 | 5/2007 | Campbell et al. | |
| 2007/0282269 A1 | 12/2007 | Carter et al. | |
| 2008/0004515 A1 | 1/2008 | Jennewine | |
| 2008/0051738 A1 | 2/2008 | Griffin | |
| 2008/0114304 A1 | 5/2008 | Nalesso et al. | |
| 2008/0172028 A1 | 7/2008 | Blomquist | |
| 2008/0243211 A1 | 10/2008 | Cartwright et al. | |
| 2008/0294040 A1 | 11/2008 | Mohiuddin et al. | |
| 2009/0024083 A1 | 1/2009 | Kriesel et al. | |
| 2009/0062767 A1 | 3/2009 | Van Antwerp et al. | |
| 2009/0198215 A1 | 8/2009 | Chong et al. | |
| 2009/0278875 A1 | 11/2009 | Holm et al. | |
| 2009/0326472 A1 | 12/2009 | Carter et al. | |
| 2010/0036326 A1 | 2/2010 | Matusch | |
| 2010/0152658 A1 | 6/2010 | Hanson et al. | |
| 2010/0241066 A1 | 9/2010 | Hansen et al. | |
| 2010/0249706 A1* | 9/2010 | Clemente | A61M 5/14566 604/154 |
| 2011/0054399 A1 | 3/2011 | Chong et al. | |
| 2011/0073620 A1 | 3/2011 | Verrilli | |
| 2011/0144586 A1 | 6/2011 | Michaud et al. | |
| 2011/0180480 A1 | 7/2011 | Kloeffel et al. | |
| 2011/0230833 A1 | 9/2011 | Landman et al. | |
| 2012/0078161 A1 | 3/2012 | Masterson et al. | |
| 2012/0172804 A1* | 7/2012 | Plumptre | A61M 5/14566 604/154 |
| 2012/0172817 A1 | 7/2012 | Bruggemann et al. | |
| 2012/0209207 A1 | 8/2012 | Gray et al. | |
| 2013/0006213 A1 | 1/2013 | Arnitz et al. | |
| 2013/0017099 A1 | 1/2013 | Genoud | |
| 2013/0064701 A1 | 3/2013 | Konishi | |
| 2013/0177455 A1 | 7/2013 | Kamen et al. | |
| 2013/0178803 A1 | 7/2013 | Raab | |
| 2013/0237915 A1* | 9/2013 | Barrelli | A61M 5/148 604/136 |
| 2013/0245545 A1 | 9/2013 | Arnold et al. | |
| 2013/0267932 A1 | 10/2013 | Franke et al. | |
| 2013/0296792 A1 | 11/2013 | Cabiri | |
| 2014/0018730 A1 | 1/2014 | Muller-Pathle | |
| 2014/0127048 A1 | 5/2014 | Dilanni et al. | |
| 2014/0128839 A1 | 5/2014 | Dilanni et al. | |
| 2014/0142508 A1 | 5/2014 | Dilanni et al. | |
| 2014/0148784 A1 | 5/2014 | Anderson et al. | |
| 2014/0171901 A1 | 6/2014 | Langsdorf et al. | |
| 2015/0041498 A1 | 2/2015 | Kakiuchi et al. | |
| 2015/0051487 A1 | 2/2015 | Uber et al. | |
| 2015/0057613 A1 | 2/2015 | Clemente et al. | |
| 2015/0064036 A1 | 3/2015 | Eberhard | |
| 2015/0137017 A1 | 5/2015 | Ambrosina et al. | |
| 2015/0202386 A1 | 7/2015 | Brady et al. | |
| 2015/0290389 A1 | 10/2015 | Nessel | |
| 2015/0297825 A1 | 10/2015 | Focht et al. | |
| 2016/0008549 A1 | 1/2016 | Plumptre et al. | |
| 2016/0025544 A1 | 1/2016 | Kamen | |
| 2016/0055842 A1 | 2/2016 | Defranks et al. | |
| 2016/0082242 A1 | 3/2016 | Burton et al. | |
| 2016/0129190 A1 | 5/2016 | Haitsuka | |
| 2016/0193423 A1 | 7/2016 | Bilton | |
| 2016/0213851 A1 | 7/2016 | Weibel et al. | |
| 2017/0021096 A1 | 1/2017 | Cole et al. | |
| 2017/0021137 A1 | 1/2017 | Cole | |
| 2017/0100541 A1 | 4/2017 | Constantineau et al. | |
| 2017/0216516 A1 | 8/2017 | Dale | |
| 2017/0239415 A1 | 8/2017 | Hwang et al. | |
| 2017/0290975 A1 | 10/2017 | Barmaimon et al. | |
| 2018/0021521 A1 | 1/2018 | Sanchez | |
| 2018/0185579 A1 | 7/2018 | Joseph et al. | |
| 2018/0304029 A1* | 10/2018 | Koch | A61M 5/1454 |
| 2018/0313346 A1 | 11/2018 | Oakes | |
| 2019/0192782 A1 | 6/2019 | Pedersen et al. | |
| 2019/0365993 A1 | 12/2019 | Staub et al. | |
| 2020/0009315 A1 | 1/2020 | Brouet et al. | |
| 2020/0345931 A1 | 11/2020 | Gray et al. | |

FOREIGN PATENT DOCUMENTS

| | | | |
|---|---|---|---|
| CN | 102498292 | B | 7/2015 |
| CN | 204972511 | U | 1/2016 |
| CN | 105764543 | B | 7/2016 |
| CN | 206175149 | U | 5/2017 |
| CN | 107096091 | A | 8/2017 |
| CN | 108472441 | A | 8/2018 |
| DE | 4200595 | A1 | 7/1993 |
| DE | 19723648 | C1 | 8/1998 |
| DE | 102005040344 | A1 | 3/2007 |
| EP | 0454331 | A1 | 10/1991 |
| EP | 0789146 | A1 | 8/1997 |
| EP | 867196 | A2 | 9/1998 |
| EP | 1065378 | A2 | 1/2001 |
| EP | 1177802 | A1 | 2/2002 |
| EP | 1403519 | A1 | 3/2004 |
| EP | 2397181 | A1 | 12/2011 |
| EP | 2468338 | A1 | 6/2012 |
| EP | 2703024 | A1 | 3/2014 |
| EP | 1874390 | B1 | 10/2014 |
| EP | 2830499 | A1 | 2/2015 |
| FR | 2096275 | A5 | 2/1972 |
| FR | 2455269 | A1 | 11/1980 |
| FR | 2507637 | A1 | 12/1982 |
| FR | 2731475 | A1 | 9/1996 |
| GB | 357139 | A | 9/1931 |
| GB | B10488 | A | 3/1959 |
| GB | 875034 | A | 8/1961 |
| GB | 1204836 | A | 9/1970 |
| GB | 2008806 | A | 6/1979 |
| GB | 2077367 | A | 12/1981 |
| GB | 2456681 | A | 7/2009 |
| GB | 2549750 | A | 11/2017 |
| IL | 46017 | A | 11/1977 |
| JP | 06063133 | A | 3/1994 |
| JP | H06296690 | A | 10/1994 |
| JP | H08238324 | A | 9/1996 |
| JP | 2004247271 | A | 9/2004 |
| JP | 2004274719 | A | 9/2004 |
| JP | 2005188355 | A | 7/2005 |
| JP | 2006159228 | A | 6/2006 |
| JP | 6098988 | B2 | 9/2006 |
| JP | 2006249130 | A | 9/2006 |
| JP | 2009514580 | A | 4/2009 |
| JP | 2017513577 | A | 6/2017 |
| NL | 1019126 | C1 | 4/2003 |
| WO | 8101658 | A1 | 6/1981 |
| WO | 8606796 | A1 | 11/1986 |
| WO | 9320864 | A1 | 10/1993 |

(56) References Cited

FOREIGN PATENT DOCUMENTS

| | | | |
|---|---|---|---|
| WO | 9415660 | A1 | 7/1994 |
| WO | 9855073 | A1 | 12/1998 |
| WO | 9856293 | A1 | 12/1998 |
| WO | 9910040 | A1 | 3/1999 |
| WO | 9910049 | A1 | 3/1999 |
| WO | 9962576 | A1 | 12/1999 |
| WO | 0029047 | A1 | 5/2000 |
| WO | 0178812 | A1 | 10/2001 |
| WO | 0220073 | A2 | 3/2002 |
| WO | 0226282 | A2 | 4/2002 |
| WO | 2002076535 | A1 | 4/2002 |
| WO | 2003097133 | A1 | 4/2002 |
| WO | 02068823 | A1 | 9/2002 |
| WO | 2004032994 | A2 | 4/2004 |
| WO | 2004056412 | A2 | 7/2004 |
| WO | 2004110526 | A1 | 12/2004 |
| WO | 2007066152 | A2 | 6/2007 |
| WO | 2008133702 | A1 | 11/2008 |
| WO | 2009039203 | A2 | 3/2009 |
| WO | 2009141005 | A1 | 11/2009 |
| WO | 2010022069 | A2 | 2/2010 |
| WO | 2010077279 | A1 | 7/2010 |
| WO | 2010139793 | A1 | 12/2010 |
| WO | 2011010198 | A2 | 1/2011 |
| WO | 2011031458 | A1 | 3/2011 |
| WO | 2011069935 | A2 | 6/2011 |
| WO | 2011075042 | A1 | 6/2011 |
| WO | 2011133823 | A1 | 10/2011 |
| WO | 2012073032 | A1 | 6/2012 |
| WO | 2013050535 | A2 | 4/2013 |
| WO | 2013137893 | A1 | 9/2013 |
| WO | 2013149186 | A1 | 10/2013 |
| WO | 2014029416 | A1 | 2/2014 |
| WO | 2014149357 | A1 | 9/2014 |
| WO | 2014179774 | A1 | 11/2014 |
| WO | 2015032772 | A1 | 3/2015 |
| WO | 2015048791 | A1 | 4/2015 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2017148855 | A1 | 9/2017 |
| WO | 2017187177 | A1 | 11/2017 |
| WO | 2021016452 | A1 | 1/2021 |

OTHER PUBLICATIONS

Lind et al. "Linear Motion Miniature Actuators." Paper presented at the 2nd Tampere International Conference on Machine Automation, Tampere, Finland (Sep. 1998).

Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.

Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante et al., "Design, Modeling, and Performance of a High Force Piezoelectric Inchworm Motor," Journal of Intelligent Material Systems and Structures, vol. 10, 962-972 (1999).

International Search Report and Written Opinion for International Application No. PCT/US2017/055054, mailed on Jan. 25, 2018, 13 pages.

International Search Report and Written Opinion for International Application No. PCT/US2018/045155, mailed on Oct. 15, 2018, 15 pages.

International Preliminary Report on Patentability for International Application No. PCT/US2017/034811 issued on Nov. 27, 2018, 10 pages.

International Preliminary Report on Patentability for International Patent Application No. PCT/US2017/046508, Feb. 12, 2019, 10 pages.

International Search Report and Written Opinion for International Application No. PCT/US2017/046508, mailed on Jan. 17, 2018, 14 pages.

International Search Report and Written Opinion for International Application No. PCT/US2017/046777, mailed on Dec. 13, 2017, 14 pages.

International Search Report and Written Opinion for International Application No. PCT/US2017/046737, mailed on Dec. 14, 2017, 11 pages.

International Search Report and Written Opinion for International Application No. PCT/US2017/034814, mailed on Oct. 11, 2017, 18 pages.

European Search Report and Written Opinion for the European Patent Application No. EP19177571, dated Oct. 30, 2019, 8 pages.

International Preliminary Report on Patentability for International Patent Application No. PCT/US2018/014351, dated Jul. 23, 2019, 7 pages.

International Preliminary Report on Patentability for International Patent Application No. PCT/US2017/046777, dated Feb. 19, 2019, 8 pages.

International Preliminary Report on Patentability for International Patent Application No. PCT/US2017/046737, dated Feb. 19, 2019, 8 pages.

International Preliminary Report on Patentability for International Patent Application No. PCT/US2017/055054, dated Apr. 9, 2019, 8 pages.

International Search Report and Written Opinion for Application No. PCT/US2017/034811, mailed Oct. 18, 2017, 15 pages.

EPO Search Report received in Application No. 13768938.6, dated Nov. 11, 2015, 8 pages.

International Search Report and Written Opinion for PCT Application No. PCT/US13/34674, mailed Aug. 6, 2013, 17 pages.

International Search Report and Written Opinion for International Application No. PCT/GB2007/004073, Jan. 31, 2008, 8 pages.

International Search Report and Written Opinion for International Patent Application No. PCT/US2019/063615, dated May 3, 2020, 17 pages.

International Preliminary Report on Patentability for International Patent Application No. PCT/US2018/045155, dated Feb. 14, 2020, 10 pages.

International Search Report and Written Opinion for International Patent Application No. PCT/US2019/035756, dated Jul. 31, 2019, 11 pages.

International Search Report and Written Opinion for PCT Application No. PCT/US2019/059854, mailed Aug. 26, 2020, 15 pages.

International Search Report and Written Opinion, Application No. PCT/US2022/016713, mailed Aug. 5, 2022, 19 bages.

International Search Report and Written Opinion for International Patent Application No. PCT/US2022/029012, mailed Aug. 19, 2022, 12 pages.

European Search Report and Written Opinion for European Patent Application No. EP20174878, dated Sep. 29, 2020, 8 pages.

Schott web-page image from Jul. 9, 2016, https://www.US.schott.com/pharmaceutical_packaging/english/products/cartridges.html.

International Search Report and Written Opinion for International Patent Application No. PCT/US2021/055581, dated Feb. 8, 2022, 19 pages.

International Search Report and Written Opinion for International Patent Application No. PCT/US2022/011356, dated Apr. 29, 2022, 19 pages.

* cited by examiner

FLEXIBLE LINKAGE FOR POSITIVE DISPLACEMENT PUMPS

RELATED APPLICATIONS

This application claims the benefit of U.S. Provisional Patent Application No. 63/256,712, filed Oct. 18, 2021, the contents of which are incorporated herein by reference in their entirety.

BACKGROUND

Many conventional automatic drug delivery systems are well known, including, for example, wearable drug delivery devices of the type shown in FIG. 2. The drug delivery device 102 can be designed to deliver any type of liquid drug to a user. In specific embodiments, the drug delivery device 102 can be, for example, an OmniPod® drug delivery device manufactured by Insulet Corporation of Acton, Massachusetts. The drug delivery device 100 can be a drug delivery device such as those described in U.S. Pat. Nos. 7,303,549, 7,137,964, or 6,740,059, each of which is incorporated herein by reference in its entirety.

FIG. 3 illustrates an exemplary drug delivery device 102 of the type shown in FIG. 2 with the cover removed. Drug delivery device 102 typically includes a positive displacement pump mechanism which includes a reservoir 302 that stores the liquid drug. The liquid drug stored in the reservoir 302 may be delivered to the user by expelling the drug from reservoir 302 using a driven plunger 304 that longitudinally translates through reservoir 302 to force the liquid drug through a fluid port defined in the reservoir. The plunger 304 may be longitudinally translated through the reservoir 302 by, for example, a driven leadscrew.

An exemplary prior art pump mechanism 400 is shown in perspective view in FIG. 4A and in cross-sectional view in FIG. 4B. Pump mechanism 400 may comprise a drive mechanism 402 capable of providing a rotational motion which will cause a tube nut 406 to rotate. Tube nut 406 is in threaded engagement with leadscrew 404 such that when tube nut 406 is rotated by drive mechanism 402, leadscrew 404 moves in a longitudinal direction toward a distal end of reservoir 302. Because leadscrew 404 is coupled to plunger 304, longitudinal movement of leadscrew 404 will cause plunger 304 to move longitudinally within reservoir 302. FIGS. 4A and 4B show reservoir 302 in an empty state, wherein plunger 304 is positioned against the distal end wall of reservoir 302. FIG. 4C shows reservoir 302 in a full state, wherein plunger 304 is positioned at a proximal end of reservoir 302. Note that, when the reservoir 302 is in a full or partially-full state, leadscrew 404 must occupy space 408, shown in FIG. 4B.

One limitation of this design is that the total footprint of the reservoir 302 and drive mechanism 402 is greater than the length of reservoir 302 by as much as 2 times. This is due to the fact that the leadscrew 404 needs to reach all the way into reservoir 302 when reservoir 302 is in the empty state (i.e., it must be approximately equal to the length of reservoir 302 minus the space taken by plunger 304). When reservoir 302 is full, leadscrew 404 will necessarily extend behind reservoir 302 to occupy space 408 at a length up to the length of the reservoir.

In wearable, on-body devices, it is desirable to keep the pump mechanism 400, as well as the overall drug delivery device 102, as small as possible to minimize the impact to the wearer. Therefore, it would be desirable to replace the prior art pump mechanism 400 with a positive displacement pump mechanism having a different method of driving the plunger 304 within the reservoir 302 that does not require the large footprint of the prior art pump mechanism 400. This would reduce the size footprint of pump mechanism 400, thereby improving the size impact of the overall drug delivery system 102 while maintaining the benefits of the pumping methodology. Further, a smaller pump mechanism would enable the use of a larger reservoir capable of holding larger quantities of the liquid drug.

DEFINITIONS

As used herein, the term "liquid drug" should be interpreted to include any drug in liquid form capable of being administered by a drug delivery device via a subcutaneous cannula, including, for example, insulin or co-formulations of two or more of GLP-1, pramlintide, and insulin.

SUMMARY

Embodiments of the invention disclosed herein include a size-optimized pump mechanism having a flexible linkage between a drive mechanism and a plunger disposed in a reservoir, wherein the flexible linkage comprises, in a preferred embodiment, a coiled metal tape that unrolls and pushes on the plunger, causing a longitudinal translation of the plunger within the reservoir to dispense a liquid drug from the reservoir. The flexible linkage has one end attached to the plunger through an open end of the reservoir with the remainder of the flexible linkage being initially coiled around a reel. As the flexible linkage is uncoiled from the reel, it passes through a pair of rollers shaped to provide the flexible linkage with a curved cross-sectional shape to increase the structural integrity and the buckling force of the flexible linkage, thus allowing it to impart force on the plunger required to cause the longitudinal translation of the plunger through the reservoir to force the liquid drug in the reservoir to a patient interface. At least one roller of the pair of rollers is driven by a drive mechanism and the flexible linkage is uncoiled by virtue of a frictional engagement with the rollers.

DETAILED DESCRIPTION

This disclosure presents various systems, components and methods for moving a liquid drug, from a reservoir 302 in a wearable drug delivery device 102 to a patient interface, typically a needle or cannula. The embodiments described herein provide one or more advantages over conventional, prior art systems, components and methods.

Various embodiments of the present invention include systems and methods for delivering a medication to a user using a drug delivery device (sometimes referred to herein as a "pod"), either autonomously, or in accordance with a wireless signal received from an electronic device. In various embodiments, the electronic device may be a user device comprising a smartphone, a smart watch, a smart necklace, a module attached to the drug delivery device, or any other type or sort of electronic device that may be carried by the user or worn on the body of the user and that executes an algorithm that computes the times and dosages of delivery of the medication.

For example, the user device may execute an "artificial-pancreas" algorithm that computes the times and dosages of delivery of insulin. The user device may also be in communication with a sensor, such as a glucose sensor, that collects data on a physical attribute or condition of the user, such as a glucose level. The sensor may be disposed in or on the body of the user and may be part of the drug delivery device or may be a separate device.

Alternatively, the drug delivery device may be in communication with the sensor in lieu of or in addition to the communication between the sensor and the user device. The communication may be direct (if, e.g., the sensor is integrated with or otherwise a part of the drug delivery device) or remote/wireless (if, e.g., the sensor is disposed in a different housing than the drug delivery device). In these embodiments, the drug delivery device contains computing hardware (e.g., a processor, memory, firmware, etc.) that executes some or all of the algorithm that computes the times and dosages of delivery of the medication.

Figure 1:
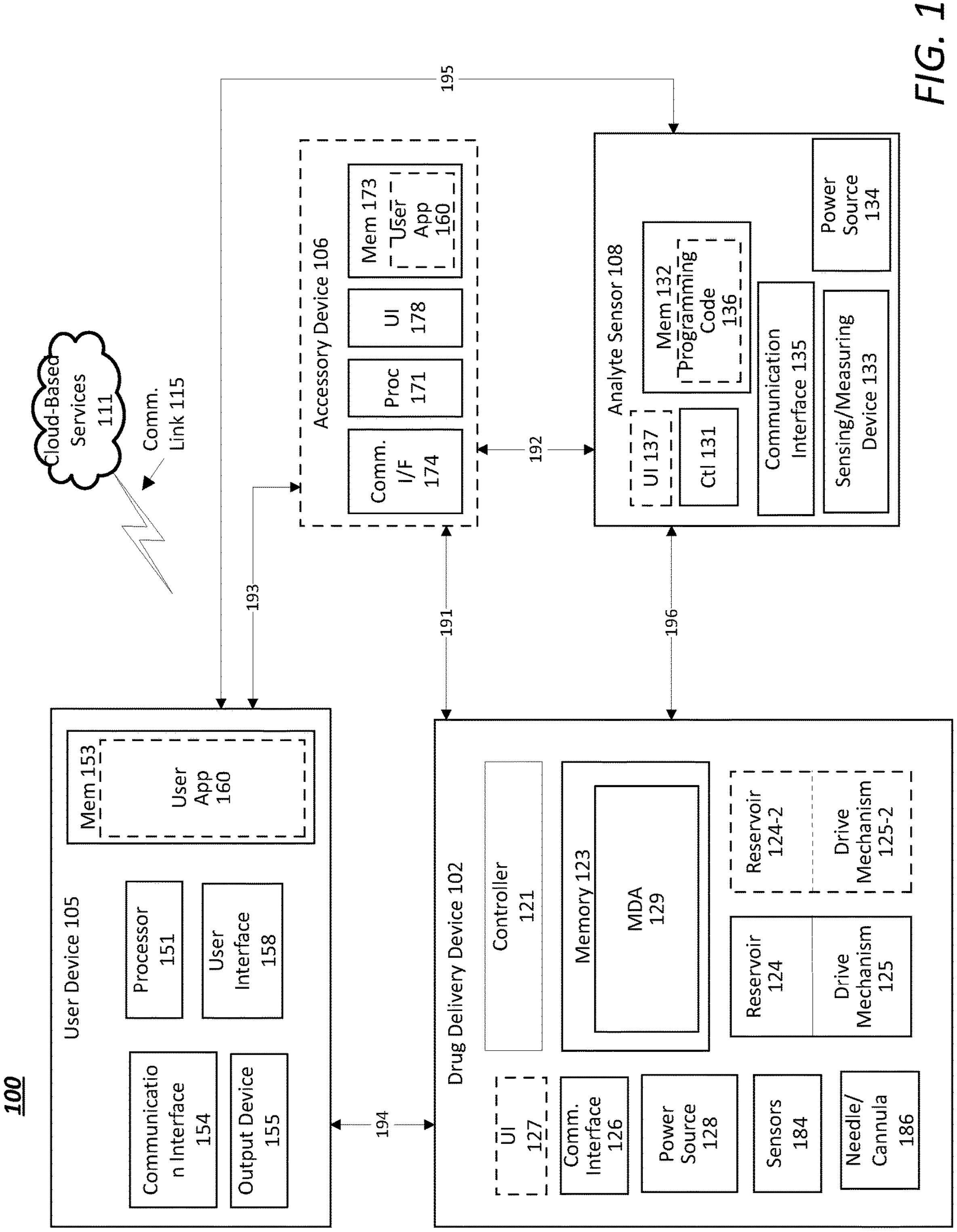
FIG. 1 illustrates a functional block diagram of an exemplary system suitable for implementing the embodiments of the invention disclosed herein.

FIG. 1 illustrates a functional block diagram of an exemplary drug delivery system 100 suitable for implementing the systems and methods described herein. The drug delivery system 100 may implement (and/or provide functionality for) a medication delivery algorithm, such as an artificial pancreas (AP) application, to govern or control the automated delivery of a drug or medication, such as insulin, to a user (e.g., to maintain euglycemia—a normal level of glucose in the blood). The drug delivery system 100 may be an automated drug delivery system that may include a drug delivery device 102 (which may be wearable), an analyte sensor 108 (which may also be wearable), and a user device 105.

Drug delivery system 100, in an optional example, may also include an accessory device 106, such as a smartwatch, a personal assistant device, or the like, which may communicate with the other components of system 100 via either a wired or wireless communication links 191-193.

User Device

The user device 105 may be a computing device such as a smartphone, a tablet, a personal diabetes management (PDM) device, a dedicated diabetes therapy management device, or the like. In an example, user device 105 may include a processor 151, device memory 153, a user interface 158, and a communication interface 154. The user device 105 may also contain analog and/or digital circuitry that may be implemented as a processor 151 for executing processes based on programming code stored in device memory 153, such as user application 160 to manage a user's blood glucose levels and for controlling the delivery of the drug, medication, or therapeutic agent to the user, as well for providing other functions, such as calculating carbohydrate-compensation dosage, a correction bolus dosage and the like as discussed below. The user device 105 may be used to program, adjust settings, and/or control operation of drug delivery device 102 and/or the analyte sensor 103 as well as the optional smart accessory device 106.

The processor 151 may also be configured to execute programming code stored in device memory 153, such as the user app 160. The user app 160 may be a computer application that is operable to deliver a drug based on information received from the analyte sensor 103, the cloud-based services 111 and/or the user device 105 or optional accessory device 106. The memory 153 may also store programming code to, for example, operate the user interface 158 (e.g., a touchscreen device, a camera or the like), the communication interface 154 and the like. The processor 151, when executing user app 160, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described herein.

In a specific example, when the user app 160 is an AP application, the processor 151 is also configured to execute a diabetes treatment plan (which may be stored in a memory) that is managed by user app 160. In addition to the functions mentioned above, when user app 160 is an AP application, it may further provide functionality to determine a carbohydrate-compensation dosage, a correction bolus dosage and determine a basal dosage according to a diabetes treatment plan. In addition, as an AP application, user app 160 provides functionality to output signals to the drug delivery device 102 via communications interface 154 to deliver the determined bolus and basal dosages.

The communication interface 154 may include one or more transceivers that operate according to one or more radio-frequency protocols. In one embodiment, the transceivers may comprise a cellular transceiver and a Bluetooth® transceiver. The communication interface 154 may be configured to receive and transmit signals containing information usable by user app 160.

User device 105 may be further provided with one or more output devices 155 which may be, for example, a speaker or a vibration transducer, to provide various signals to the user.

Drug Delivery Device

In various exemplary embodiments, drug delivery device 102 may include a reservoir 124 and drive mechanism 125, which are controllable by controller 121, executing a medication delivery algorithm (MDA) 129 stored in memory 123. Alternatively, controller 121 may act to control reservoir 124 and drive mechanism 125 based on signals received from user app 160 executing on a user device 105 and communicated to drug delivery device 102 via communication link 194. Drive mechanism 125 operates to longitudinally translate a plunger through the reservoir, such as to force the liquid drug through an outlet fluid port to needle/cannula 186.

In an alternate embodiment, drug delivery device 102 may also include an optional second reservoir 124-2 and second drive mechanism 125-2 which enables the independent delivery of two different liquid drugs. As an example, reservoir 124 may be filled with insulin, while reservoir 124-2 may be filled with Pramlintide or GLP-1. In some embodiments, each of reservoirs 124, 124-2 may be configured with a separate drive mechanism 125, 125-2, respectively, which may be separately controllable by controller 121 under the direction of MDA 129. Both reservoirs 124, 124-2 may be connected to a common needle/cannula 186.

Drug delivery device 102 may be optionally configured with a user interface 127 providing a means for receiving input from the user and a means for outputting information to the user. User interface 127 may include, for example, light-emitting diodes, buttons on a housing of drug delivery device 102, a sound transducer, a micro-display, a microphone, an accelerometer for detecting motions of the device or user gestures (e.g., tapping on a housing of the device) or any other type of interface device that is configured to allow a user to enter information and/or allow drug delivery device 102 to output information for presentation to the user (e.g., alarm signals or the like).

Drug delivery device 102 includes a patient interface 186 for interfacing with the user to deliver the liquid drug. Patient interface may be, for example, a needle or cannula for delivering the drug into the body of the user (which may be done subcutaneously, intraperitoneally, or intravenously). Drug delivery device 102 further includes a mechanism for inserting the needle/cannula 186 into the body of the user, which may be integral with or attachable to drug delivery device 102. The insertion mechanism may comprise, in one embodiment, an actuator that inserts the needle/cannula 186 under the skin of the user and thereafter retracts the needle, leaving the cannula in place.

In one embodiment, drug delivery device 102 includes a communication interface 126, which may be a transceiver that operates according to one or more radio-frequency protocols, such as Bluetooth®, Wi-Fi, near-field communication, cellular, or the like. The controller 121 may, for example, communicate with user device 105 and an analyte sensor 108 via the communication interface 126.

In some embodiments, drug delivery device 102 may be provided with one or more sensors 184. The sensors 184 may include one or more of a pressure sensor, a power sensor, or the like that are communicatively coupled to the controller 121 and provide various signals. For example, a pressure sensor may be configured to provide an indication of the fluid pressure detected in a fluid pathway between the patient interface 186 and reservoir 124. The pressure sensor may be coupled to or integral with the actuator for inserting the patient interface 186 into the user. In an example, the controller 121 may be operable to determine a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount. In one embodiment, analyte sensor 108 may be integral with drug delivery device 102.

Drug delivery device 102 further includes a power source 128, such as a battery, a piezoelectric device, an energy harvesting device, or the like, for supplying electrical power to controller 121, memory 123, drive mechanisms 125 and/or other components of drug delivery device 102.

Drug delivery device 102 may be configured to perform and execute processes required to deliver doses of the medication to the user without input from the user device 105 or the optional accessory device 106. As explained in more detail, MDA 129 may be operable, for example, to determine an amount of insulin to be delivered, JOB, insulin remaining, and the like and to cause controller 121 to activate drive mechanism 125 to deliver the medication from reservoir 124. MDA 129 may take as input data received from the analyte sensor 108 or from user app 160.

The reservoirs 124, 124-2 may be configured to store drugs, medications or therapeutic agents suitable for automated delivery, such as insulin, Pramlintide, GLP-1, co-formulations of insulin and GLP-1, morphine, blood pressure medicines, chemotherapy drugs, fertility drugs or the like.

Drug delivery device 102 may be a wearable device and may be attached to the body of a user, such as a patient or diabetic, at an attachment location and may deliver any therapeutic agent, including any drug or medicine, such as insulin or the like, to a user at or around the attachment location. A surface of drug delivery device 102 may include an adhesive to facilitate attachment to the skin of a user.

When configured to communicate with an external device, such as the user device 105 or the analyte sensor 108, drug delivery device 102 may receive signals over the wired or wireless link 194 from the user device 105 or from the analyte sensor 108. The controller 121 of drug delivery device 102 may receive and process the signals from the respective external devices as well as implementing delivery of a drug to the user according to a diabetes treatment plan or other drug delivery regimen.

Accessory Device

Optional accessory device 107 may be, a wearable smart device, for example, a smart watch (e.g., an Apple Watch®), smart eyeglasses, smart jewelry, a global positioning system-enabled wearable, a wearable fitness device, smart clothing, or the like. Similar to user device 105, the accessory device 107 may also be configured to perform various functions including controlling drug delivery device 102. For example, the accessory device 107 may include a communication interface 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the user app 160, or a pared-down version of user app 160 with reduced functionality. In some instances, accessory device 107 may also include sensors of various types.

Analyte Sensor

The analyte sensor 108 may include a controller 131, a memory 132, a sensing/measuring device 133, an optional user interface 137, a power source/energy harvesting circuitry 134, and a communication interface 135. The analyte sensor 108 may be communicatively coupled to the processor 151 of the management device 105 or controller 121 of drug delivery device 102. The memory 132 may be configured to store information and programming code 136.

The analyte sensor 108 may be configured to detect multiple different analytes, such as glucose, lactate, ketones, uric acid, sodium, potassium, alcohol levels or the like, and output results of the detections, such as measurement values or the like. The analyte sensor 108 may, in an exemplary embodiment, be configured to measure a blood glucose value at a predetermined time interval, such as every 5 minutes, every 1 minute, or the like. The communication interface 135 of analyte sensor 108 may have circuitry that operates as a transceiver for communicating the measured blood glucose values to the user device 105 over a wireless link 195 or with drug delivery device 102 over the wireless communication link 108. While referred to herein as an analyte sensor 108, the sensing/measuring device 133 of the analyte sensor 108 may include one or more additional sensing elements, such as a glucose measurement element, a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121 of drug delivery device 102, the controller 131 of the analyte sensor 108 may be operable to perform many functions. For example, the controller 131 may be configured by programming code 136 to manage the collection and analysis of data detected by the sensing and measuring device 133.

Although the analyte sensor 108 is depicted in FIG. 1 as separate from drug delivery device 102, in various embodiments, the analyte sensor 108 and drug delivery device 102 may be incorporated into the same unit. That is, in various examples, the analyte sensor 108 may be a part of and integral with drug delivery device 102 and contained within the same housing as drug delivery device 102 or an attachable housing thereto. In such an example configuration, the controller 121 may be able to implement the functions required for the proper delivery of the medication alone without any external inputs from user device 105, the cloud-based services 111, another sensor (not shown), the optional accessory device 106, or the like.

Cloud-Based Services

Drug delivery system 100 may communicate with or receive services from cloud-based services 111. Services provided by cloud-based services 111 may include data storage that stores personal or anonymized data, such as blood glucose measurement values, historical IOB or TDI, prior carbohydrate-compensation dosage, and other forms of data. In addition, the cloud-based services 111 may process anonymized data from multiple users to provide generalized information related to TDI, insulin sensitivity, IOB and the like. The communication link 115 that couples the cloud-based services 111 to the respective devices 102, 105, 106, 108 of system 100 may be a cellular link, a Wi-Fi link, a Bluetooth® link, or a combination thereof.

Communication Links

The wireless communication links 115 and 191-196 may be any type of wireless link operating using known wireless communication standards or proprietary standards. As an example, the wireless communication links 191-196 may provide communication links based on Bluetooth®, Zigbee®, Wi-Fi, a near-field communication standard, a cellular standard, or any other wireless protocol via the respective communication interfaces 126, 135, 154 and 174.

Operational Example

In an operational example, user application 160 implements a graphical user interface that is the primary interface with the user and is used to start and stop drug delivery device 102, program basal and bolus calculator settings for manual mode as well as program settings specific for automated mode (hybrid closed-loop or closed-loop).

User app 160, provides a graphical user interface 158 that allows for the use of large text, graphics, and on-screen instructions to prompt the user through the set-up processes and the use of system 100. It will also be used to program the user's custom basal insulin delivery profile, check the status, of drug delivery device 102, initiate bolus doses of insulin, make changes to a patient's insulin delivery profile, handle system alerts and alarms, and allow the user to switch between automated mode and manual mode.

User app 160 may configured to operate in a manual mode in which user app 160 will deliver insulin at programmed basal rates and bolus amounts with the option to set temporary basal profiles. The controller 121 will also have the ability to function as a sensor-augmented pump in manual mode, using sensor glucose data provided by the analyte sensor 108 to populate the bolus calculator.

User app 160 may configured to operate in an automated mode in which user app 160 supports the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the user app 160 for insulin dosing parameters. The insulin dosing parameters will be adapted over time based on the total daily insulin (TDI) delivered during each use of drug delivery device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

The user app 160 (or MDA 129) may provide periodic insulin micro-boluses based upon past glucose measurements and/or a predicted glucose over a prediction horizon (e.g., 60 minutes). Optimal post-prandial control may require the user to give meal boluses in the same manner as current pump therapy, but normal operation of the user app 160 will compensate for missed meal boluses and mitigate prolonged hyperglycemia. The user app 160 uses a control-to-target strategy that attempts to achieve and maintain a set target glucose value, thereby reducing the duration of prolonged hyperglycemia and hypoglycemia.

In some embodiments, user device 105 and the analyte sensor 108 may not communicate directly with one another. Instead, data (e.g., blood glucose readings) from analyte sensor may be communicated to drug delivery device 102 via link 196 and then relayed to user device 105 via link 194. In some embodiments, to enable communication between analyte sensor 108 and user device 105, the serial number of the analyte sensor must be entered into user app 160.

User app 160 may provide the ability to calculate a suggested bolus dose through the use of a bolus calculator. The bolus calculator is provided as a convenience to the user to aid in determining the suggested bolus dose based on ingested carbohydrates, most-recent blood glucose readings (or a blood glucose reading if using fingerstick), programmable correction factor, insulin to carbohydrate ratio, target glucose value and insulin on board (IOB). IOB is estimated by user app 160 taking into account any manual bolus and insulin delivered by the algorithm.

DESCRIPTION OF EMBODIMENTS

In primary embodiments of the invention, the reservoir and pump are integrated into a single component (referred to herein as a "pump mechanism") and the linkage between the drive mechanism of the prior art pump mechanism and the reservoir of the prior art pump mechanism is replaced by a novel flexible linkage as described herein which reduces the overall size of the footprint of the pump mechanism, or, alternatively, allows for the use of a larger reservoir.

Figure 5A:
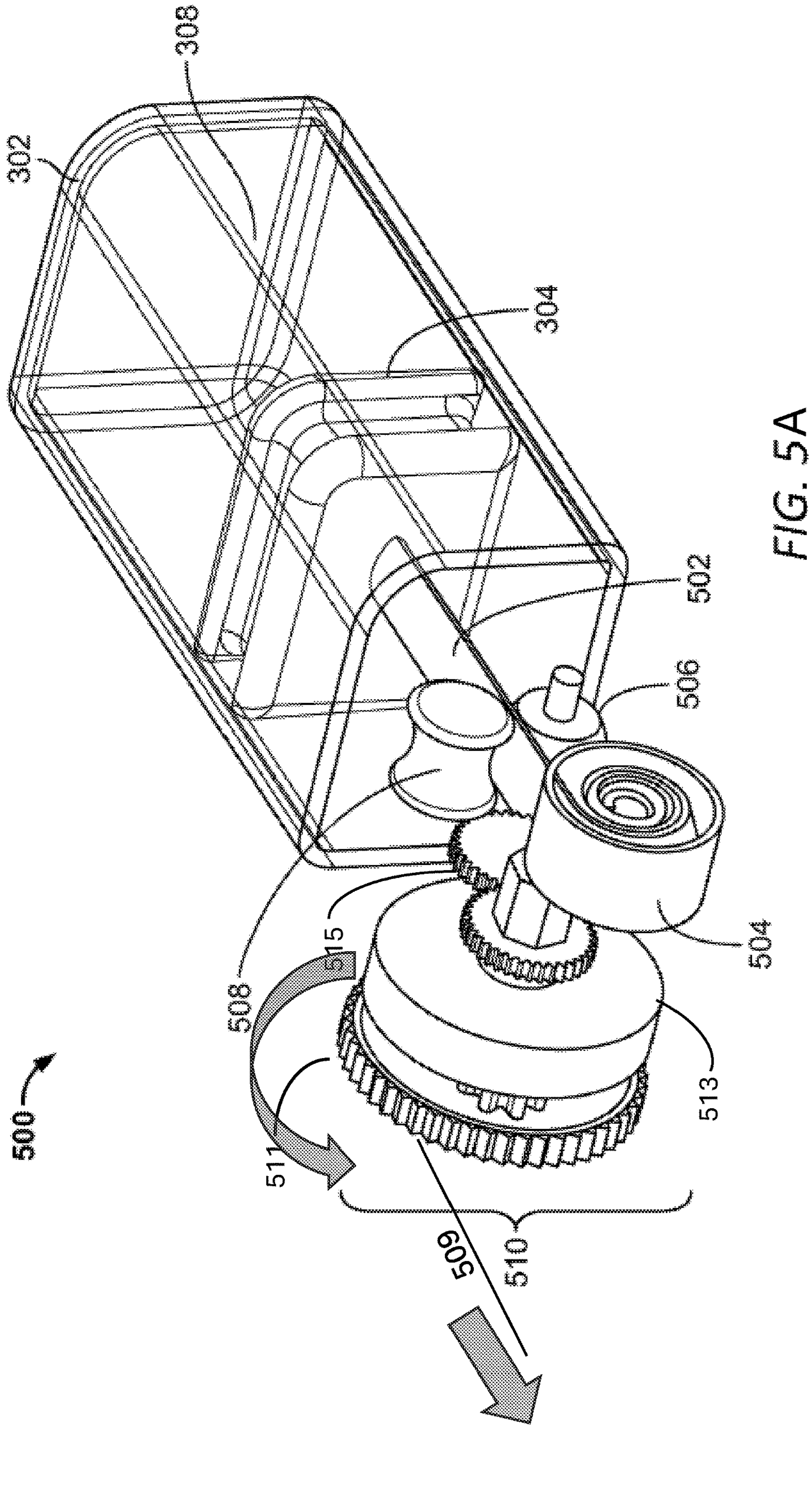
FIG. 5 is a perspective view of the pump mechanism of the present invention, showing the novel flexible linkage between the drive mechanism and the plunger.
Figure 5B:
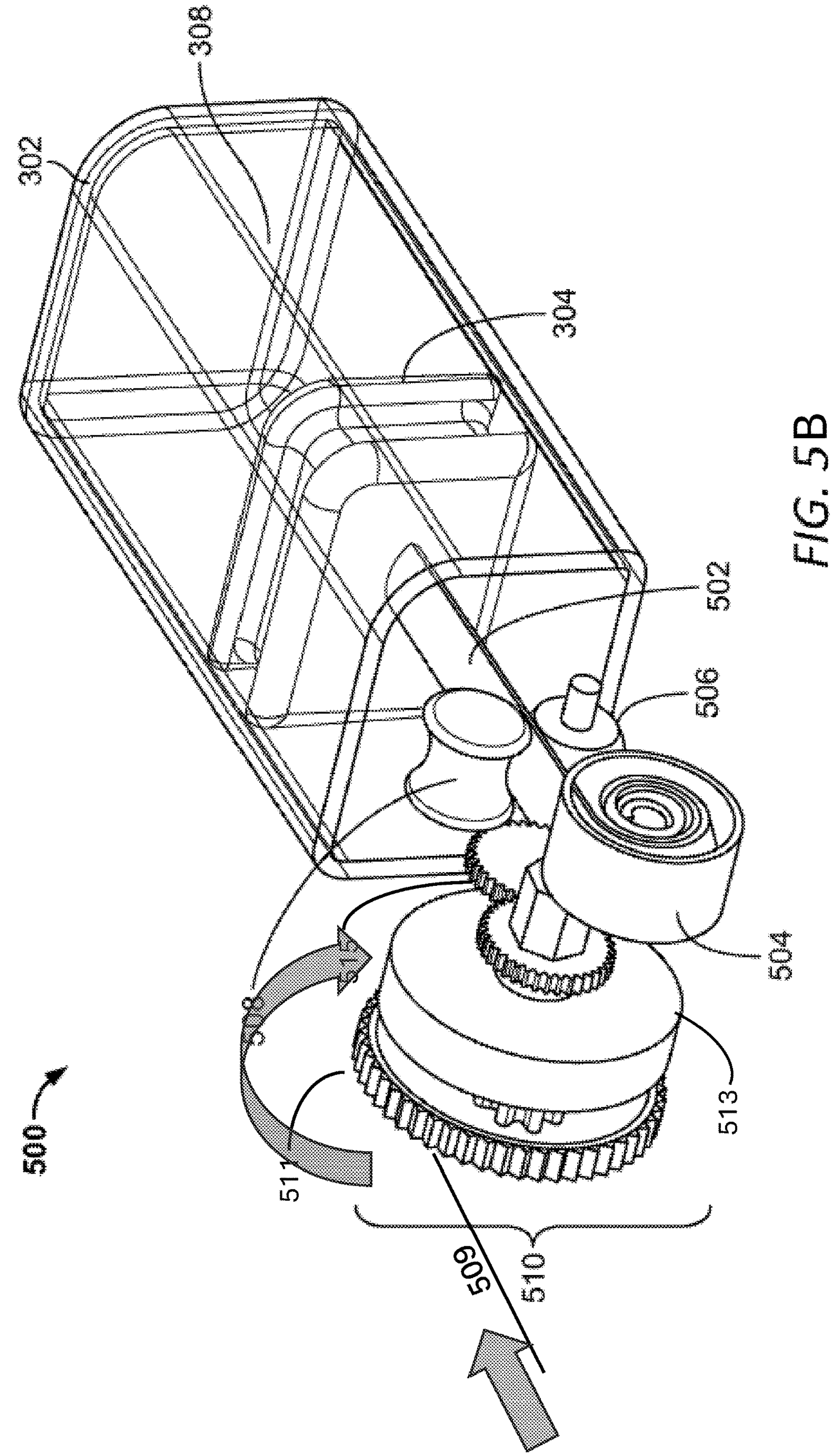
Figure 5C:
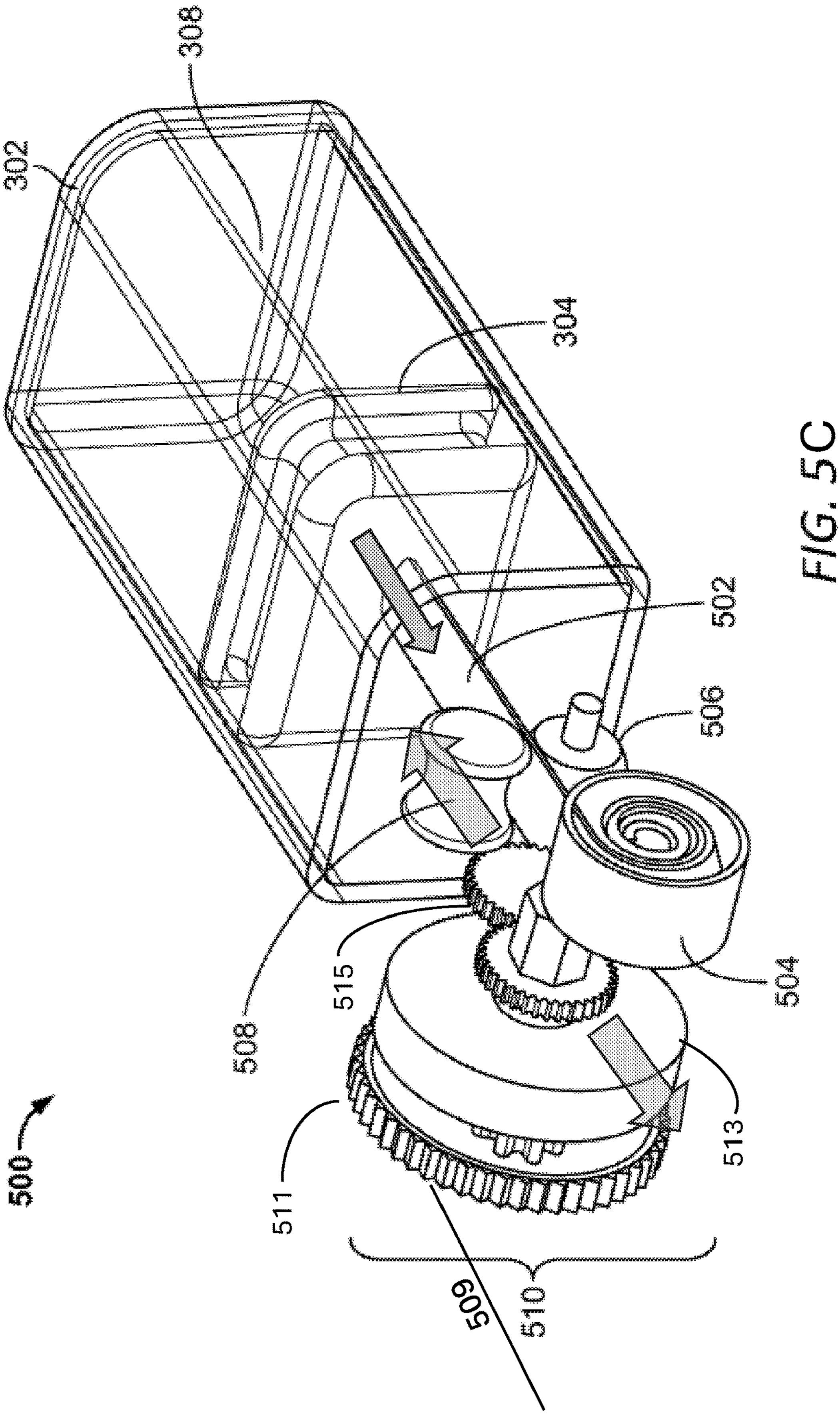
Figure 6:
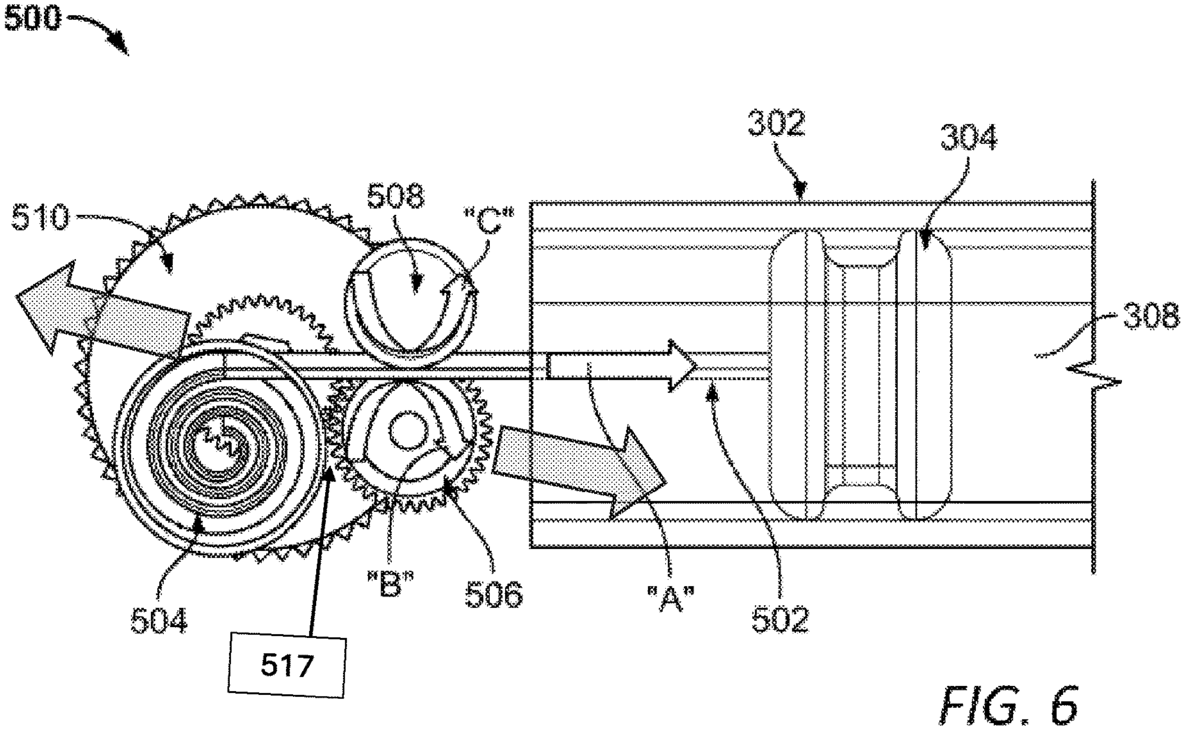
FIG. 6 is a side view of the pump mechanism of FIG. 5, showing the direction of travel of rollers and the flexible linkage.

Embodiments of the pump mechanism 500 described herein are shown in FIG. 5 and FIG. 6 and comprise various components including a reservoir 302, a plunger 304, configured to translate longitudinally through the interior of reservoir 302, a drive mechanism 508 and a flexible linkage 502 between the drive mechanism and the plunger 304. In the described embodiments, the reservoir 302 may comprise a tube-like structure having a proximal, open end and a distal, closed-end, wherein the closed-end is configured with a fluid path (not shown) such as to allow the liquid drug disposed in area 308 between the plunger and the closed end of the reservoir 302 to be forced through the fluid path to a patient interface.

Figure 2:
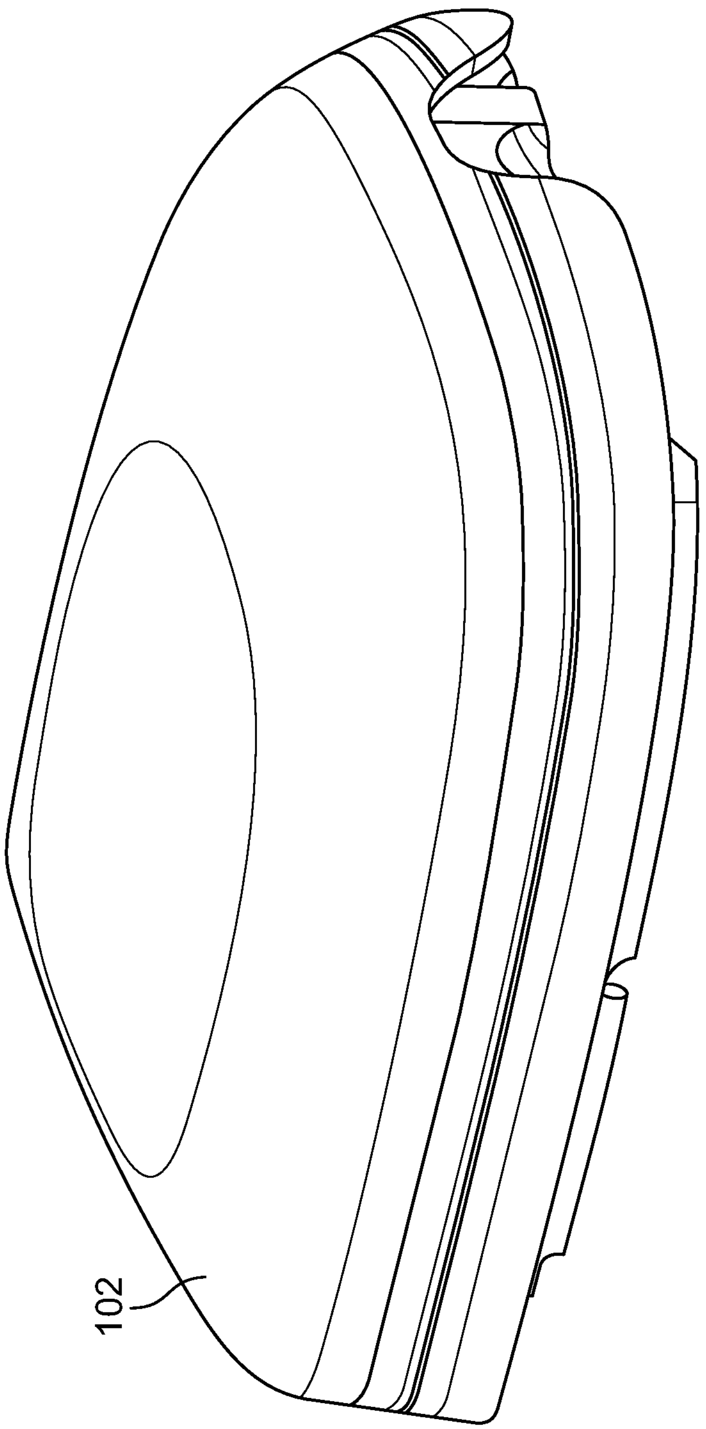
FIG. 2 is a perspective view of a prior art wearable drug delivery device of the type with which the present invention may be used.
Figure 3:
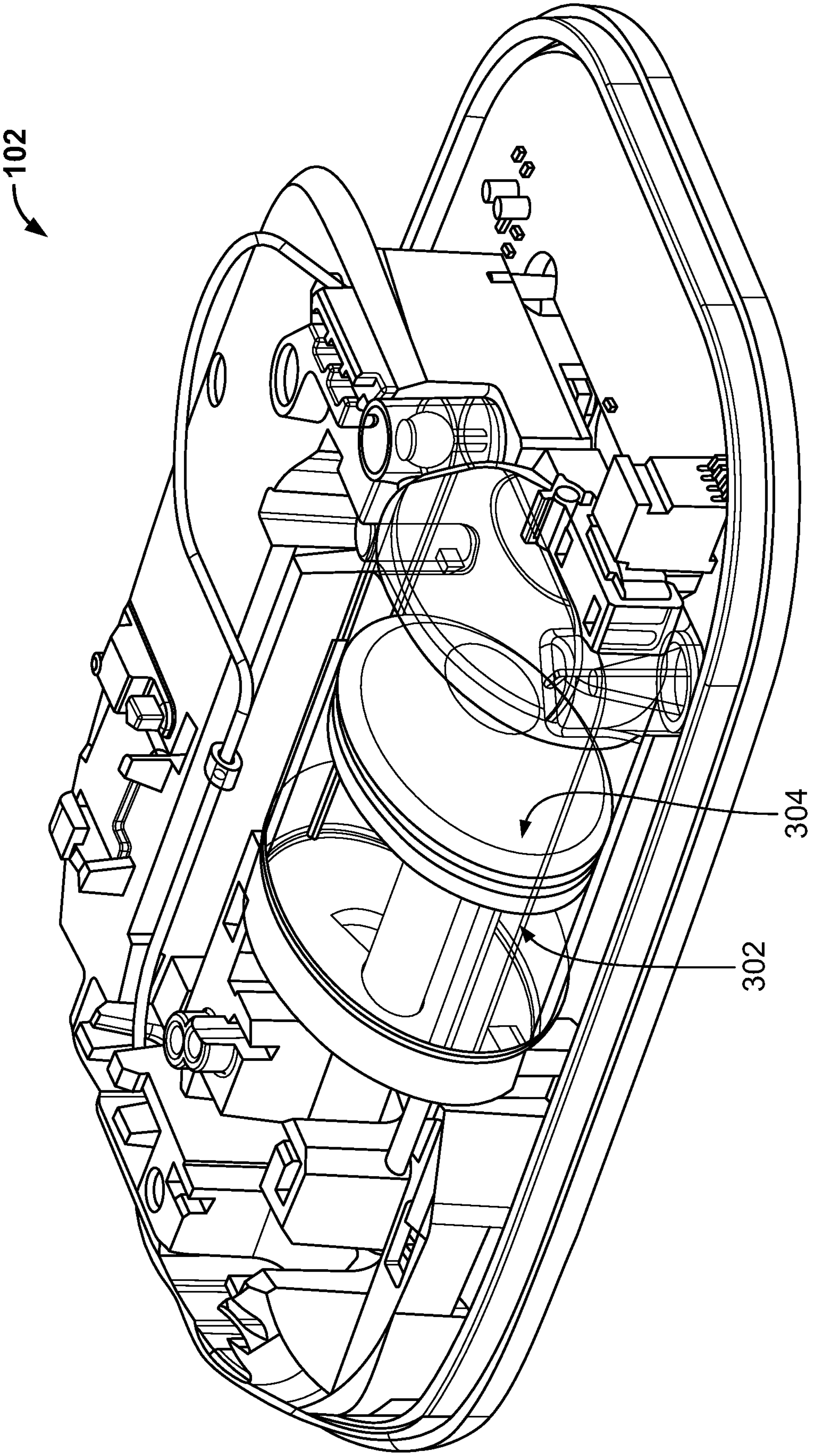
FIG. 3 is a perspective view of the prior art wearable drug delivery device of FIG. 2 having the cover removed to reveal the arrangement of internal parts.
Figure 4A:
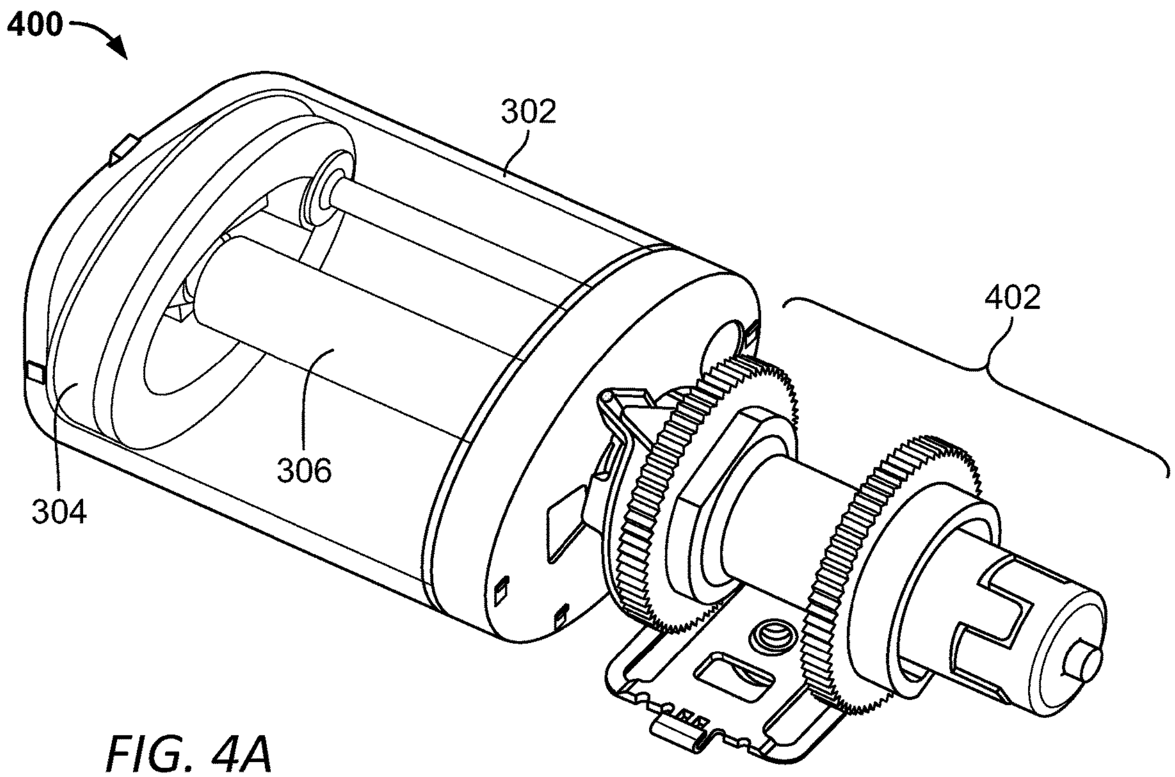
FIG. 4A is a perspective view of a prior art pump mechanism utilized in the drug delivery device of FIG. 2, showing the positioning of various parts of the pump mechanism when the reservoir is in an empty state.
Figure 4B:
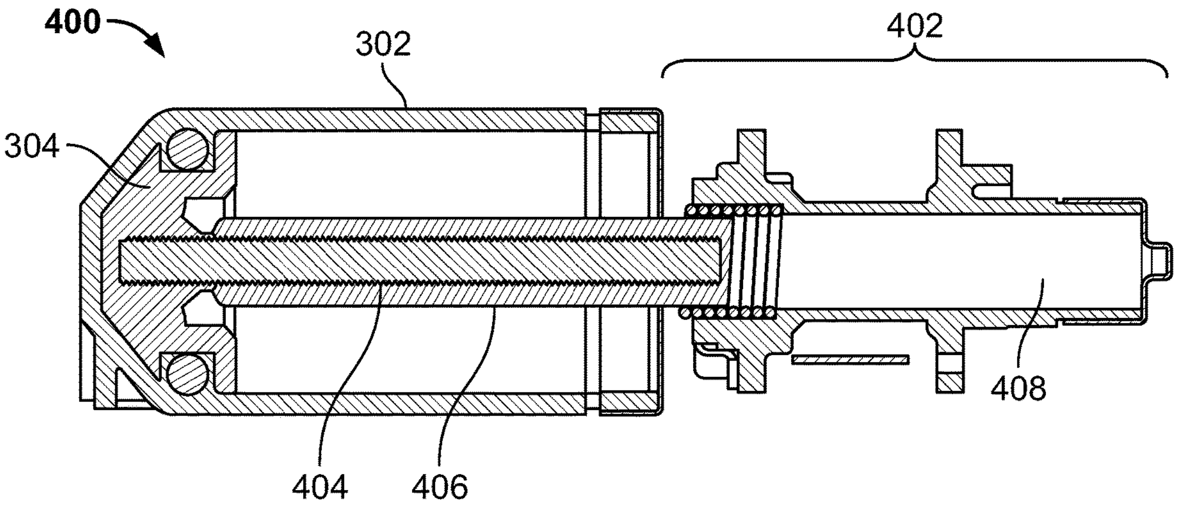
FIG. 4B is a cross-sectional view of the prior art pump mechanism of FIG. 4A showing the positioning of the leadscrew responsible for moving the plunger within the reservoir.
Figure 4C:
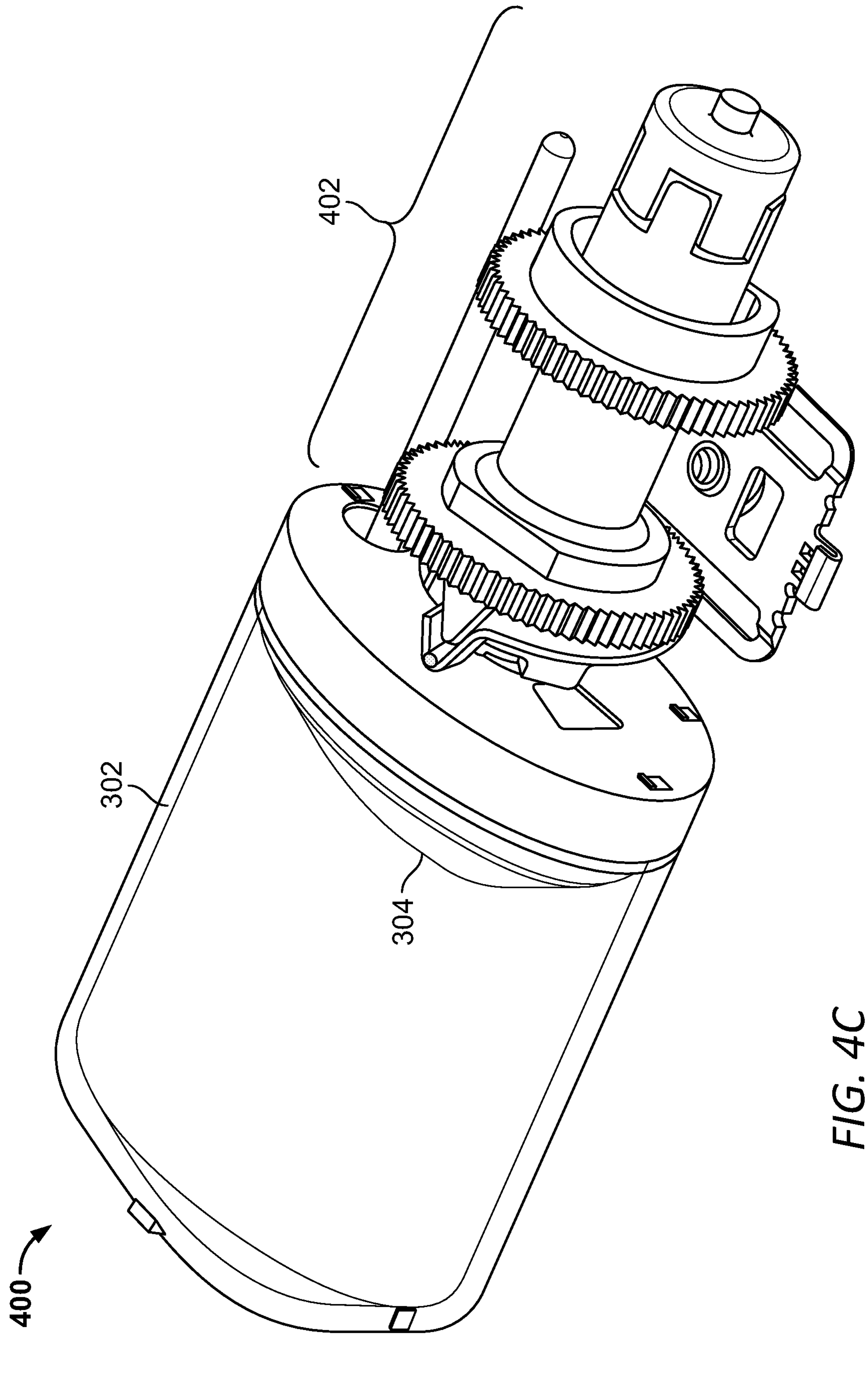
FIG. 4C is a perspective view of the prior art pump mechanism of FIG. 4A showing the positioning of various parts of the pump mechanism when the reservoir is in a full state.

The reservoir 302 may, in various embodiments of the invention, be composed of polyethylene or an injection-molded plastic, but, in other embodiments, may be composed of any material impermeable to the liquid drug disposed therein. The plunger 304 may be composed of any material and may be configured with one or more O-rings along one or more circumferential surfaces thereof such as to create a seal between the plunger 304 and the interior wall of reservoir 302 when the plunger 304 is disposed within reservoir 302. The cross-sectional area of the reservoir 302 and plunger 304 may be of any convenient shape, such as to be able to take advantage of all available space within one or more housings of drug delivery device 102, which, as shown in FIG. 2, may be configured with curved portions.

A primary embodiment of the invention is shown in a perspective view in FIG. 5 and in a side view in FIG. 6 and illustrates pump mechanism 500 provided as part of a drug delivery device 102 for delivery of a liquid drug to a user.

Reservoir 302 stores the liquid drug prior to delivery to the user. In some embodiments, the drug delivery device 102 may come with a prefilled reservoir containing the liquid drug. In other embodiments, the reservoir 302 may be filled by or refillable by the user. Reservoir 302 may be fitted with a plunger 304 which is longitudinally translatable through the interior length of reservoir 302 in direction "A" as shown in FIG. 6. The liquid drug is stored in area 308 of reservoir 302 between plunger 304 and the distal end of reservoir 302.

Longitudinal translation of plunger 304 toward the distal end of reservoir 308 will force the liquid drug from area 308 via a fluid port (not shown) to a patient interface, typically a subcutaneous needle or cannula (not shown). The fluid port may be provided with a one-way valve that prevents fluids from the user from entering area 308 of reservoir 302. The fluid port may be located at any point such as to be in fluid communication with space 308 within reservoir 302, however, in preferred embodiments, the fluid port is located as close to the distal end of reservoir 302 as possible to avoid wasting any holdup volume of the liquid drug that would otherwise get trapped at the distal end of the reservoir 302. Preferably, reservoir 302 is rigidly attached to the body of the drug delivery device.

The longitudinal translation of the plunger 304 in direction "A" toward the distal end of reservoir 302, in the preferred embodiments, is accomplished via a flexible linkage 402 between a drive mechanism 410 and plunger 304. As flexible linkage 502 is uncoiled from reel 504, it passes through a pair of rollers comprising a roller 506 having a convex circumferential surface and a roller 508 having a concave circumferential surface, which impart flexible linkage 502 with a curved cross-sectional shape as it is passed therethrough, to add structural strength and to prevent buckling of flexible linkage 502 as it pushes plunger 504 toward the distal end of reservoir 302. Flexible linkage 502 may be uncoiled from reel 504 by virtue of a frictional engagement between flexible linkage 502 and rollers 506, 508. Alternatively, a motor or drive mechanism (such as drive mechanism 510) may be directly coupled to reel 504 to uncoil flexible linkage 502 therefrom. In one embodiment of the invention, flexible linkage 502 is composed of steel; however, other materials may be used.

In preferred embodiments of the invention, convex roller 506 may be driven by drive mechanism 510 in a clockwise direction "B" as shown in FIG. 6. Concave roller 508 is preferably spring-loaded to force concave roller 508 into contact with flexible linkage 502 to provide a frictional engagement between flexible linkage 502 and both of rollers 506, 508. Concave roller 508 counter-rotates with respect to convex-surfaced roller 506 in a counterclockwise direction "C" as shown in FIG. 6. The frictional engagement of rollers 506 and 508 with flexible linkage 502 provides the force necessary to uncoil the flexible linkage 502 from reel 504 and push the flexible linkage 502 against a rear surface of plunger 304 such as to cause plunger 304 to translate longitudinally within reservoir 402 to dispense the liquid drug. In one embodiment of the invention, rollers 506, 508 are composed of polyethylene or an injection-molded plastic; however, other material may be used.

In preferred embodiments of the invention, convex-surfaced roller 506 is driven by drive mechanism 510, which may comprise, in one embodiment, a ratchet mechanism 511 and a set of reduction gears. The gear reduction would ensure that each pulse of the ratchet mechanism would dispense the required volume of the liquid drug. In one embodiment of the invention, drive mechanism 510 may include a planetary gear assembly 513; however, any arrangement of gears may be used.

In certain embodiments, drive mechanism 510 may be provided with a clutch mechanism 517 such as to be able to disengage drive mechanism 510 from driven roller 506 or 508 to allow rollers 506, 508 to move in a reverse direction. This is useful in embodiments of drug delivery device 102 wherein reservoir 302 may be filled by the user via injection of the liquid drug through a fill port, thus causing plunger 304 to move in a direction opposite direction "A" in FIG. 6 (longitudinally toward the open end of reservoir 302), thereby causing flexible linkage 502 to re-coil about reel 504. Because rollers 506, 508 are able to rotate in either direction, the quantity of the liquid drug deposited into or dispensed from reservoir 302 may be calculated as a function of the number of rotations or partial rotations of either of rollers 506, 508. A sensor may be provided for the purpose of tallying the rotations.

In alternate embodiments of the invention, as would be realized by one of skill in the art, roller 506 may be provided with the concave circumferential surface and roller 508 may be provided with the convex circumferential surface. Also, in alternative embodiments, roller 508 may be driven by drive mechanism 510 and roller 506 may be spring-loaded against flexible linkage 502.

In various aspects of the primary embodiment, either or both of rollers 506, 508 could be provided with rubber coatings on the circumferential surfaces thereof to aid in the provision of the frictional engagement with flexible linkage 502.

Figure 7:
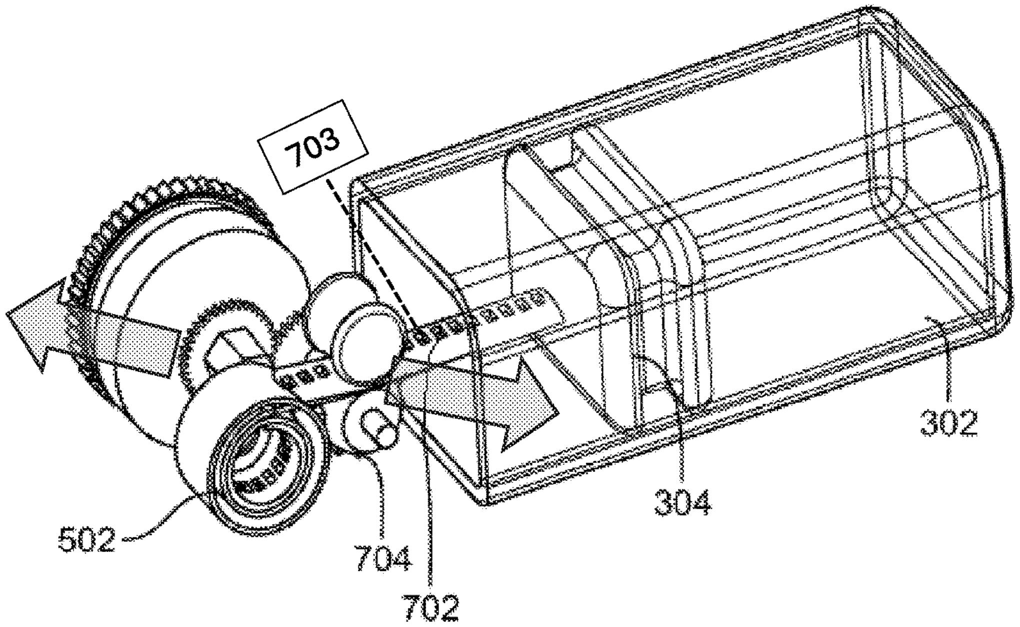
FIG. 7 is a perspective view of an alternate embodiment of the invention wherein the flexible linkage is provided with a series of holes engaging protrusions on the rollers.

In an alternate embodiment shown in FIG. 7, flexible linkage 502 may be provided with a series of holes 702 corresponding to protrusions 704 on either (or both) of rollers 506, 508, depending on which of roller 506, 508 is driven by drive mechanism 510, wherein the protrusions rotationally engage the holes to provide improved linear translation of flexible linkage 502.

In yet another alternative embodiment, a light sensor 703 could be provided to add the capability to tally the holes 702 in flexible linkage 502 as they pass over the light sensor, thereby providing a measurement of how much of the flexible linkage 502 has been uncoiled from reel 504. This may serve as an indication of how far the plunger has translated longitudinally toward the distal end of reservoir 302. Additionally, the quantity of the liquid drug deposited into or dispensed from reservoir 302 may be calculated as a function of the tally of the holes 702 in flexible linkage 502 passing over the light sensor.

Drive mechanism 510 may be actuated by a motor or, alternatively, by the expansion and contraction of a wire 509 composed of a shape memory alloy, such as Nitinol. Additionally, drive mechanism 510 may be located in alternative positions with respect to reservoir 302 to those shown in FIGS. 5-6 and connected to driven roller 506 via a gear train linkage 515.

In yet another embodiment of the invention, flexible linkage 502, instead of being coiled around reel 504, could be coiled around either driven roller 506 or spring-loaded roller 508. In such cases, as the flexible linkage 502 unrolls from the coil, the radius of the coil would change. The change in the linear travel of flexible linkage 502 could be calculated based on the reducing radius of the coil and the motion of drive mechanism 510 adjusted accordingly.

The following examples pertain to various embodiments of the pump mechanism suitable for use in a wearable drug delivery device:

Example 1 is a first embodiment of a pump mechanism comprising a reservoir, a plunger disposed in the reservoir, a drive mechanism and a flexible linkage coupling the drive mechanism and the plunger.

Example 2 is an extension of Example 1, or any other example disclosed herein, wherein the flexible linkage extends through the open end of the reservoir and is coupled to a rear surface of the plunger.

Example 3 is an extension of Example 2, or any other example disclosed herein, wherein the flexible linkage is coiled around a reel and uncoiled by motion of the drive mechanism.

Example 4 is an extension of Example 3, or any other example disclosed herein, further comprising a pair of rollers, at least one of which is rotationally driven by the drive mechanism.

Example 5 is an extension of Example 4, or any other example disclosed herein, when one of the rollers is spring-loaded against the other roller and wherein the flexible linkage is disposed between the rollers such that rotation of the rollers by the drive mechanism imparts a linear translation of the flexible linkage by virtue of a frictional engagement between the rollers and the flexible linkage.

Example 6 is an extension of Example 5, or any other example disclosed herein, wherein one of the rollers is configured with a concavely-shaped circumference and the other roller is configured with a convexly-shaped circumference such as to impart a curved cross-sectional shape to the flexible linkage.

Example 7 is an extension of Example 6, or any other example disclosed herein, wherein the linear translation of the flexible linkage through the rollers causes a linear translation of the plunger toward the closed end of the reservoir.

Example 8 is an extension of Example 7, or any other example disclosed herein, wherein one or both of the rollers is configured with a rubber-coated circumference such as to improve the frictional engagement between the rollers and the flexible linkage.

Example 9 is an extension of Example 4, or any other example disclosed herein, further comprising a series of holes defined in the flexible linkage and a series of protrusions defined on the circumference of one or both of the rollers wherein the protrusions engage the series of holes in the flexible linkage as the rollers are rotationally driven by the drive mechanism.

Example 10 is an extension of Example 9, or any other example disclosed herein, further comprising a light sensor configured to sense light passing through the holes defined in the flexible linkage.

Example 11 is an extension of Example 4, or any other example disclosed herein, wherein the flexible linkage is coiled around one of the rollers.

Example 12 is an extension of Example 4, or any other example disclosed herein, wherein the flexible linkage is coiled around a reel separate from the rollers.

Example 13 is an extension of Example 4, or any other example disclosed herein, wherein the drive mechanism comprises a ratchet wheel, a planetary gear driven by the ratchet wheel and a gear train coupled to the planetary gear for engaging the driven roller.

Example 14 is extension of Example 13, or any other example disclosed herein, wherein the ratchet wheel is rotated by an expansion and contraction of a wire composed of a shape memory alloy.

Example 15 is an extension of Example 13, or any other example disclosed herein, wherein the ratchet wheel is rotated by a motor.

Example 16 is an extension of Example 4, or any other example disclosed herein, wherein pump mechanism further comprises a clutch mechanism disposed between the drive mechanism and the driven roller.

Example 17 is an extension of Example 16, or any other example disclosed herein, wherein the position of the plunger within the reservoir can be calculated as a function of the number of rotations or partial rotations of the rollers in either direction.

Example 18 is a method for operating a positive displacement pump mechanism comprising uncoiling a flexible linkage from a reel, wherein the flexible linkage is attached to a plunger disposed in the reservoir of the positive displacement pump and wherein a linear translation of the uncoiled portion of the flexible linkage causes a linear translation of the plunger within the reservoir.

Example 19 is an extension of Example 18, or any other example disclosed herein, the method further comprising passing the uncoiled portion of the flexible linkage between a pair of rollers, one roller having a convex circumferential surface and the other roller having a concave circumferential surface wherein the rollers impart a curved cross-sectional shape of the flexible linkage.

Example 20 is an extension of Example 19, or any other example disclosed herein, the method further comprising rotating one or both of the rollers using a drive mechanism, wherein a frictional engagement between the rollers and the flexible linkage causes the flexible linkage to uncoil.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

To those skilled in the art to which the invention relates, many modifications and adaptations of the invention may be realized. Implementations provided herein, including sizes, shapes, ratings and specifications of various components or arrangements of components, and descriptions of specific manufacturing processes, should be considered exemplary only and are not meant to limit the invention in any way. As one of skill in the art would realize, many variations on implementations discussed herein which fall within the scope of the invention are possible. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A pump mechanism comprising:

a reservoir comprising a tube-like structure having a first end and a second end, the second end configured with a fluid path;

a plunger, disposed in the reservoir, the plunger configured translate longitudinally within the reservoir toward the second end;

a drive mechanism;

a pair of rollers, at least one of which is a driven roller that is rotationally driven by the drive mechanism;

a flexible linkage between the drive mechanism and the plunger; and a clutch mechanism, disposed between the drive mechanism and the driven roller, so as to enable disengagement of the drive mechanism from the driven roller and rotation of the pair of rollers in a reverse direction.

2. The pump mechanism of claim 1, wherein the flexible linkage extends through the first end of the reservoir and is attached to a rear surface of the plunger.

3. The pump mechanism of claim 2, wherein the flexible linkage is coiled around a reel and uncoiled by motion of the drive mechanism.

4. The pump mechanism of claim 1, wherein at least one roller of the pair of rollers is biased against the other roller and further wherein the flexible linkage is disposed between the rollers such that rotation motion of the rollers by the drive mechanism imparts a linear translation of the flexible linkage by virtue of a frictional engagement between the rollers and the flexible linkage.

5. The pump mechanism of claim 4, wherein one of the rollers is configured with a concavely-shaped circumference and the other roller is configured with a convexly-shaped circumference such that passage of the flexible linkage through the rollers imparts a curved cross-sectional shape to the flexible linkage.

6. The pump mechanism of claim 5, wherein the linear translation of the flexible linkage through the rollers causes a linear translation of the plunger toward the second end of the reservoir.

7. A pump mechanism of claim 1, wherein one or both of the rollers is configured with a rubber-coated circumferential surface such as to improve a frictional engagement between the rollers and the flexible linkage.

8. The pump mechanism of claim 1, further comprising:

a series of holes defined in the flexible linkage; and a series of protrusions defined on the circumferential surface of at least one of the rollers;

wherein the series of protrusions on the roller engages the series of holes in the flexible linkage as the roller is rotationally driven by the drive mechanism.

9. The pump mechanism of claim 8, further comprising:

a light sensor configured to sense light passing through the holes defined in the flexible linkage.

10. The pump mechanism of claim 1, wherein the flexible linkage is coiled around one of the rollers.

11. The pump mechanism of claim 1, wherein the flexible linkage is coiled around a reel separate from the rollers.

12. The pump mechanism of claim 1, wherein the drive mechanism comprises:

a ratchet wheel;

a planetary gear, driven by the ratchet wheel; and a gear train, coupling the planetary gear and the driven roller.

13. The pump mechanism 12, wherein the ratchet wheel is rotated by an expansion and contraction of a wire composed of a shape memory alloy.

14. The pump mechanism 12, wherein the ratchet wheel is rotated by motor.

15. The pump mechanism of claim 1, wherein a position of the plunger within the reservoir is a function of a number of rotations or partial rotations of the rollers in either direction.

* * * * *